United States Patent [19]

Miller

[11] 4,336,710

[45] Jun. 29, 1982

[54] HARDNESS TESTER

[76] Inventor: Arthur Miller, 1602 Myrtlewood St., Costa Mesa, Calif. 92626

[21] Appl. No.: 157,533

[22] Filed: Jun. 9, 1980

[51] Int. Cl.³ .............................................. G01N 3/52
[52] U.S. Cl. ........................................................ 73/79
[58] Field of Search ........................ 73/79, 78, 11, 12; 29/271, 272; 30/364, 366, 361, 367; 408/35; 221/189, 188

[56] References Cited

U.S. PATENT DOCUMENTS 1,762,639 6/1930 Roudie ..................................... 73/79
2,001,087 5/1935 Abramson ............................... 73/12
3,038,330 6/1962 Criche ..................................... 73/79

FOREIGN PATENT DOCUMENTS 1187394 2/1965 Fed. Rep. of Germany .......... 73/79
298066 10/1928 United Kingdom ................ 221/189

Primary Examiner—Kyle L. Howell
Assistant Examiner—Denis E. Corr

[57] ABSTRACT

A hardness tester comprising a tubular element mounted in an upright position, a ball, and a retaining mechanism for the ball. A passage extends from the retaining mechanism through the tubular element and terminates in an opening adapted to be positioned over a surface of a test specimen. The tubular element has a wall through which the passage is visible from the exterior of the tubular element and indicia on the wall. The ball has a lesser cross-sectional area than the passage and a lesser cross-sectional area than the opening.

12 Claims, 6 Drawing Figures

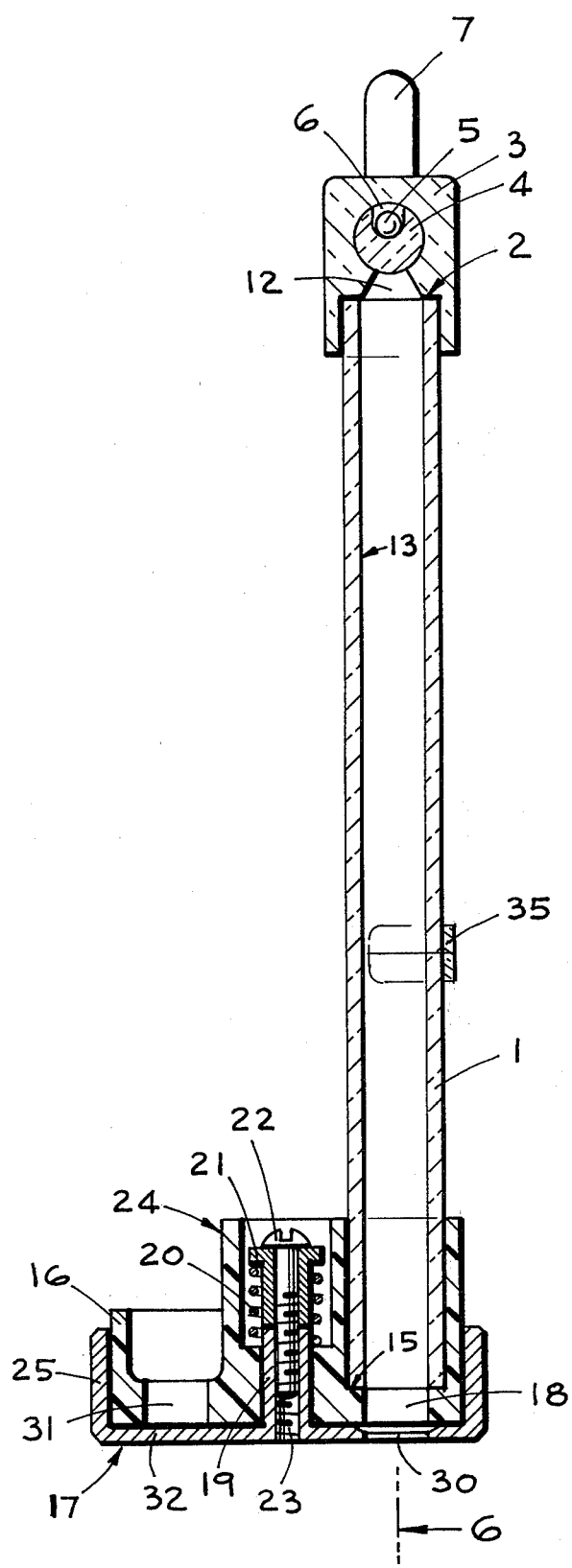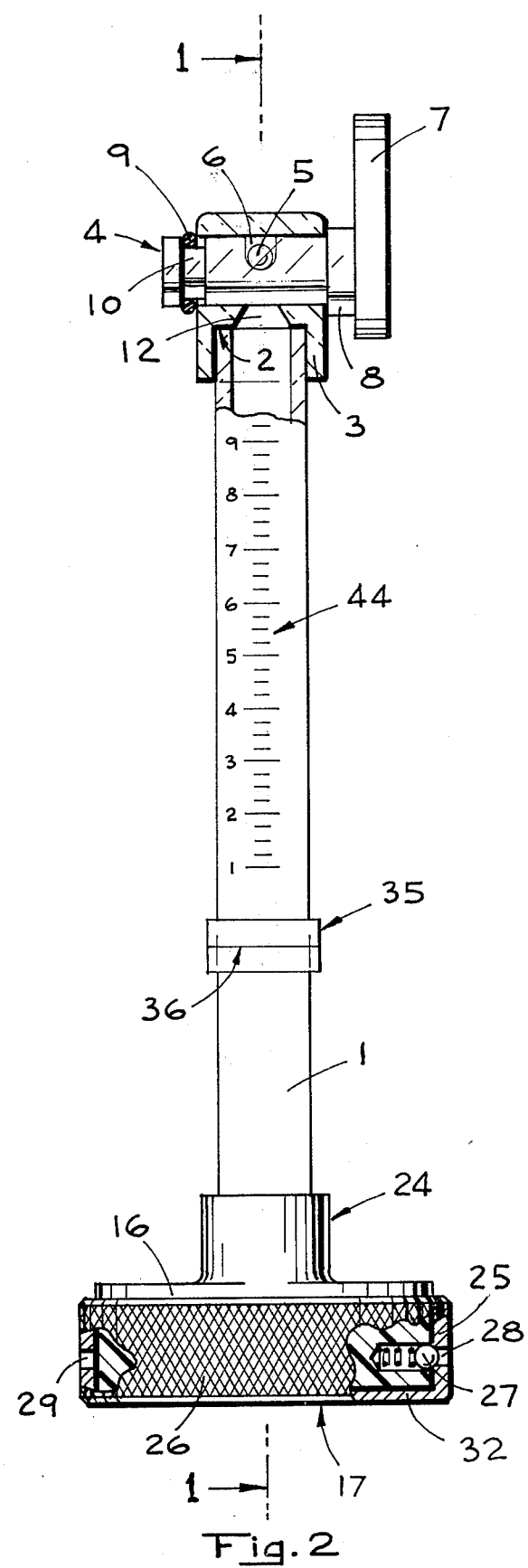

HARDNESS TESTER

BACKGROUND OF THE INVENTION

This invention relates to hardness testing devices which utilize the rebound of a falling object, sometimes referred to as a striker, from the surface of a test specimen to measure the hardness of said specimen. More particularily, this invention relates to a type of harness tester which utilizes a free falling striker contained in a vertical tubular structure with striker releasing means at the top, and striker retaining means at the bottom.

Previous hardness testers of this type have suffered from several disadvantages;

To achieve accurate hardness readouts in terms of striker rebound it is desirable that the striker be unencumbered by friction. In previous rebound type hardness testers the striker was usually operating within the confines of a closely fitting tubular structure which often resulted in inconsistent striker rebounds due to a high probability of random frictional contact between the striker and said tubular structure, this condition being aggrevated by deviations of the tubular structure from the perfectly vertical position.

To operate a rebound type hardness tester repeatedly, the striker must be returned to its release position above the test specimen. To achieve consistent rebounds of the striker, it is most desirable to release said striker with substantially zero velocity at a specific height above the test specimen. Some prior art instruments returned and released the striker by means of complex lifting and releasing mechanisms. Others, who relied on the simple expedient of returning the striker to its release position by inverting the instrument, utilized the inertia of the striker to engage it in its release position by means of spring loaded latches, levers, or cams, all of which can adversely affect the velocity of the striker at the time of release, either by accelerating the striker due to operator dexterity in overcoming spring pressure or friction of the release mechanism, or by retarding striker velocity due to friction of the striker against a fixed or movable surface of the instrument during release.

To test the hardness of small test specimens it is desirable that the mass of the striker be kept to a minimum consistent only with adequate rebound indication. Previous hardness testers employed strikers of massive proportions, their shape, size and mass being dictated by the means utilized to release and to retain said strikers.

SUMMARY OF THE INVENTION

The present invention provides a rebound type hardness tester which solves all of the above noted disadvantages and problems. The concepts of this invention are applicable to any portable hardness test instrument which can be utilized for on-site hardness tests of various specimens in terms of size and substance such as ferrous and nonferrous metals or thermoplastic and thermosetting materials.

According to the present invention a ball is released at a specific height above the test specimen and is allowed to fall into a central opening of a vertical tube with an inside dimension which is substantially larger than the diameter of the ball, thereby insuring that the ball avoids contact with the inside wall of the tube. An important advantage of this concept is that the instrument is thereby more tolerant to variations of tube size, and to deviations of the tube from the perfectly vertical position which in turn results in a significant reduction of manufacturing cost by eliminating the requirement for high precision components while maintaining a standard of accuracy which is equal to the most elaborate and expensive instruments.

The present invention provides rotatable and slidable means for releasing a ball at a specific height with substantially zero initial velocity.

The present invention further provides means for collecting said ball from the surface of a test specimen as well as means for retaining said ball within a substantially larger tube.

The present invention also provides a slidable index which cooperates with an incremental scale on said tube and aids in establishing the rebound height of the ball upon said scale which may be related to several known hardness values such as Rockwell, Brinell, and Shore.

The present invention provides visual means for ascertaining whether the instrument had been reset for the next test.

According to the present invention balls of different diameters may be used in the same instrument, thereby extending its versatility in terms of sensitivity to different specimen materials.

The present invention further provides an inexpensive hardness test instrument which is suitable for the application of known production techniques, such as thermoplastic injection molding, without in any way affecting the accuracy of the instrument.

BRIEF DESCRIPTION OF THE DRAWINGS

FIG. 1 is a sectional view of the hardness tester taken along line 1 of FIG. 2.

FIG. 2 is a fragmentary elevation of the hardness tester.

DESCRIPTION OF THE PREFERRED EMBODIMENT

Figure 3:
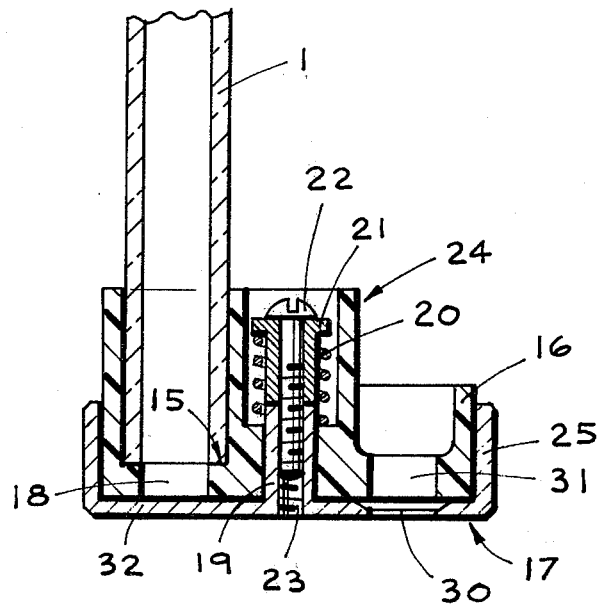
FIG. 3 is a fragmentary sectional view of the hardness tester taken along line 1 of FIG. 2, illustrating the position of the collector when rotated 180° with respect to the base.

Referring to the drawings, the hardness tester as seen in FIGS. 1 and 2 is comprised of a transparent plastic tube 1 which may be a length of commercially available extruded plastic tubing of any desired cross-section such as rectangular, triangular, and round, with an incremental vertical scale 44 thereon, said scale having indicia which are relatable to known hardness values such as Rockwell, Brinell, and Shore. The upper end of the tube 1 terminates in a recessed abutment 2 within the ball release housing 3 and may be assembled by means of adhesive bonding. For improved producibility in large quantities the tube 1 and the ball release housing 3 could be combined into a homogenuous injection-molded unit which would have the same purpose and function. The ball release housing 3, essentially a rectangular block which may be injection molded transparent plastic, has a ball release 4 of like material loosely mounted for rotation, its axis intersecting and generally transverse to the axis of the tube 1 and a certain distance above the recessed abutment 2. The ball 5 is located in a ball recess 6 within the ball release 4. Since the ball release 4 will accept balls of different sizes with equal facility, the ball recess 6 must be dimensioned to accept the largest ball with a certain amount of clearance.

One end of the ball release 4 has a transverse handle 7 and a shoulder 8 which abuts against the ball release housing 3 and provides a one way axial location for the ball release 4, alligning the ball recess 6 with the axis of the tube 1. A rubber O-ring 9 is snapped into a groove 10 of the ball release 4, securing said ball release within the ball release housing 3, said groove being axially positioned to force the O-ring against the ball release housing 3, thereby insuring that the plane of rotation of the ball recess 6 remains centered over the axis of the tube 1, as well as providing a certain amount of rotational resistance for the ball release 4, said resistance obviating a precision fit of the ball release 4 in the ball release housing 3 and enabling both parts to be assembled as molded without the expense of precision machining.

The ball 5 is seen within the ball recess 6, its open end facing upward as indicated by the generally upward pointing handle 7. When the ball release 4 is slowly rotated by means of the handle 7 until said handle is pointing generally downward, the ball 5 is allowed to fall due to gravity into the small end of the conical opening 12, said small end having a somewhat larger diameter than that of the ball 5, said conical opening being concentric with the tube axis, the large end of said conical opening matching the inside configuration of the tube 1 at the recessed abutment 2. This concept for releasing the ball 5 insures that said ball is neither accelerated nor deccelerated vertically at the time of release.

Figure 4:
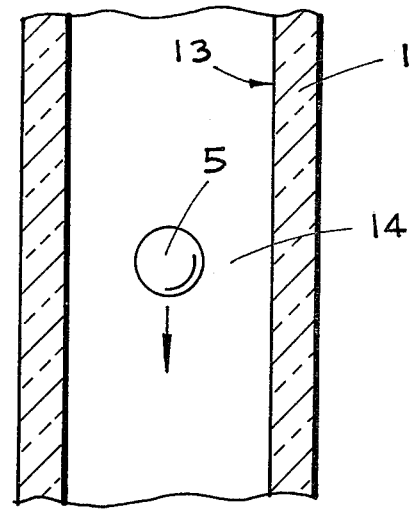
FIG. 4 is a fragmentary sectional view of the tube, illustrating the free falling ball.

To achieve repeatable rebound consistency of the ball 5 it is desirable that said ball be allowed to impact the test specimen with repeatably identical velocity. Having released the ball at a specific height above the test specimen with substantially zero velocity, the ball 5 is permitted to fall until it impacts the test specimen unencumbered by random frictional contact with the inside wall 13 of the tube 1 by means of the radial clearance 14 between said ball and the inside wall of said tube, as illustrated in FIG. 4.

The clearance 14 compensates for deviations of the instrument from the perfectly vertical position which could occur in operation if the test specimen is not perfectly level, and permits the utilization of inexpensive and loosely toleranced plastic tubing. The clearance 14 also facilitates the above mentioned one piece injection molding of the tube 1 and the ball release housing 3 which would require some tapering of the inside walls of the tube 1 for withdrawal of the core from the lower end of the tube. Said clearance (14) also eliminates the need for a full length support structure for the tube 1, such as a steel sleeve, to maintain precision in terms of tube straightness over a period of time under conditions of varying humidity and temperature.

The amount of the radial clearance 14 is a function of release height of the ball 5, the instrument's maximum expected deviation from the perfectly vertical position, and the size and dimensional tolerance of the components, and may be computed by any person skilled in the art by means of simple trigonometry.

The lower end of the tube 1 terminates in a recessed abutment 15 within the collector 16 which is mounted for rotation relative to the base 17, the axis of said recessed abutment being eccentric with respect to the axis of rotation of said collector, said recessed abutment having a hole 18 which corresponds to the inside configuration of the tube 1.

FIG. 1 illustrates the collector 16 mounted for rotation on a central shaft 19 of the base 17. Collector 16 and base 17 are assembled by means of the spring 20 which preloads the collector 16 against the base 17 to eliminate all clearance or play at the interface thereby insuring that the tube 1 remains consistently vertical, said preload being accomplished by means of the retainer 21, the screw 22, and the tapped hole 23 in the central shaft 19.

The collector 16 which may be an injection molded plastic part, has a raised boss 24 which encompasses the tube 1 and the spring 20, said raised boss providing a convenient grip surface for rotating the collector 16 with respect to the base 17. The side wall 25 of the base 17 surrounds the collector diameter with a certain amount of radial clearance, the outside diameter of said side wall having a knurled or serrated grip surface 26 thereon, the height of said side wall terminating below the upper surface of the collector 16. The collector 16 is indexed to provide two positions with respect to the base 17 by means of the spring loaded detent 27 within the collector 16, the radial location of said detent being at 90° to the centerline of the collector 16 and the tube 1, said spring loaded detent cooperating with two detent holes 28 and 29 through the side wall 25 of the base 17, said detent holes being 180° apart and on centerline of the base diameter.

The base 17 which may be an aluminum alloy screw machine part, has an eccentric hole 30, the axis of which corresponds to the axis of the tube 1, said eccentric hole having been drilled through the flat base wall 32 at 90° with respect to the axis of the detent holes 28 and 29. The collector 16 has an eccentric viewing port 31 which corresponds with the eccentric hole 30 of the base 17, said viewing port and the tube 1 being radially symmetrical about the axis of rotation of the collector 16. The viewing port 31 is used to view the test specimen therethrough, as illustrated in FIG. 3, prior to rotating the collector 16 and alligning the tube 1 with the hole 30 of the base 17 for the test, as illustrated in FIG. 1, proper allignment of the collector with respect to the base being assured by the two position indexing provision.

Figure 6:
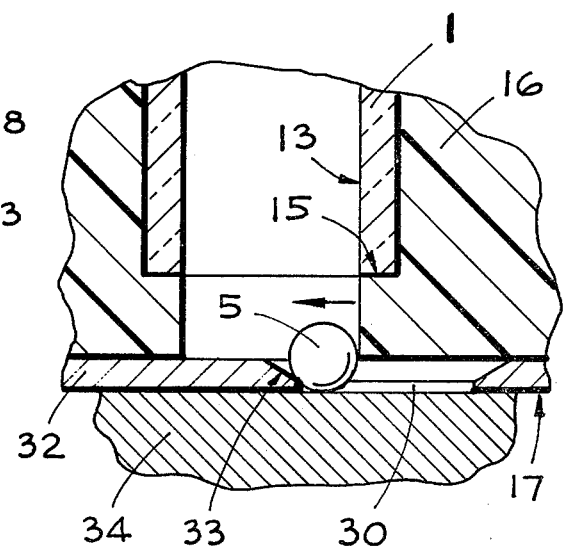
FIG. 6 is a fragmentary sectional view taken along line 6 of FIG. 1, illustrating the collection of the ball from the surface of the test specimen.

Depending upon the type of material and the method of manufacture, the thickness of the flat base wall 32 of the base 17 may be varied from approximately one tenth ball diameter to approximately one third ball diameter. Should manufacturing and material considerations dictate the use of a thicker base wall of approximately one half ball diameter, the hole 30 may be provided with a ramp 33 for proper functioning in terms of collecting the ball 5 from the surface of the test specimen 34. FIG. 6 illustrates such a ramp which in the preferred embodiment consists of a countersink 33 around the hole 30 on the inside surface of the base wall 32. If desired, different balls with diameters larger than twice the thickness of the base wall 32 can be used with equal facility in the same instrument, provided the ball recess 6 and the tube 1 are sized accordingly.

The slidable index 35 is slidably mounted on the outside of the tube 1, and is comprised of a split ring which may be made of transparent plastic with a circumferential line 36 thereon, the inside dimension of said split ring being a certain amount smaller than the outside dimension of the tube 1. When installed over the tube 1, the split ring is forced to expand within its elastic limit thereby providing a spring bias which results in friction against the tube 1, said friction resisting axial motion along said tube. The slidable index 35 is a visual aid in establishing and determining the rebound height of the ball 5 with respect to the incremental scale 44.

Figure 5:
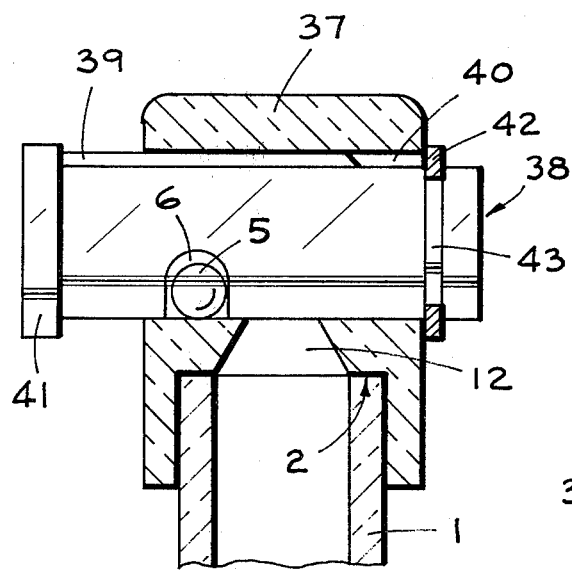
FIG. 5 is a fragmentary sectional view illustrating the slidably mounted ball release.

As I do not wish to be limited to a rotatably mounted ball release, I have provided a slidably mounted ball release as exemplified by the illustration in FIG. 5 which is comprised of: a ball release housing 37 with a recessed abutment 2 for the upper end of the tube 1, and a conical opening 12 concentric with the tube axis with a large end which corresponds to the inside configuration of the tube 1, and a small end with a diameter a certain amount larger than the diameter of the ball 5; a slidably mounted ball release 38 with a cross section which prevents rotation within the ball release housing 37 as exemplified by the key 39 and the keyway 40, the axis of said ball release intersecting and being generally transverse to the axis of the tube 1, said ball release having a shoulder 41 at one end and a snap ring 42 in a groove 43 at the opposite end, said ball release having a ball recess 6 for the ball 5, the axis of said ball recess being parallel to the axis of the tube 1, said ball recess being out of register with the small end of the conical opening 12 when the snap ring 42 abuts the ball release housing 37, said ball recess being coaxial with the small end of the conical opening 12 when the shoulder 41 abuts the ball release housing 37. The purpose and function of the illustrated slidable ball release is identical to that of the rotatably mounted ball release.

In operation the hardness tester, as described above, is placed upon the surface of a test specimen with the ball 5 seen in the ball recess 6 and the viewing port 31 alligned and indexed with the hole 30 as illustrated in FIG. 3. Having selected the test area through the viewing port 31, the operator holds the base 17 against the test specimen and rotates the collector 16 to allign the tube 1 with the hole 30 as illustrated in FIGS. 1 and 2, whereby the spring loaded detent 27 and the detent holes 29 and 28 provide the indexing by feel. The operator releases the ball 5 by rotating the handle 7, and observes the rebound height of the ball against the incremental scale 44 which may be related to known hardness values such as Rockwell, Brinell, and Shore, whereby the slidable index 35 may be used to retain the reading. Holding the base 17 against the test specimen, the operator rotates the collector 16 until the viewing port 31 is alligned and indexed with the hole 30, as in FIG. 3, thereby collecting the ball 5 and retaining it within the tube 1. Having finished the test, the operator inverts the hardness tester to permit the ball 5 to fall due to gravity into the ball recess 6, where it is visibly retained for the next test by rotating the handle 7. The hardness tester, as described above, is set up for use by a right handed operator. For use by a left handed operator, the ball release 4 may be reversed within the ball release housing 3.

The above described hardness tester is a very inexpensive test instrument, yet it compares very favorably with the most expensive hardness testers in terms of test sensitivity and accuracy.

Having shown and described the exemplary embodiments of my invention, I do not desire to be limited to the exact details of construction shown and described, for obvious modifications will occur to a person skilled in the art, without departing from the scope of this invention.

I claim:
1. A hardness tester for testing the hardness of a surface of a test specimen, said hardness tester comprising:
   a tubular element having upper and lower ends;
   means for mounting the tubular element in a generally upright position;
   a ball;
   means on said tubular element for releasably retaining said ball above said lower end;
   passage means extending from said retaining means through the tubular element and terminating in an opening adapted to be positioned over the surface of the test specimen;
   said tubular element having a wall through which the passage means is visible from the exterior of the tubular element and indicia on said wall;
   said ball having a lesser cross-sectional area than said passage means below the retaining means and a lesser cross-sectional area than said opening whereby the ball is sized to pass completely through said opening and when the ball is released from the retaining means, it falls by gravity through the passage means without touching the wall of the passage means and contacts the surface of the test specimen and rebounds from such surface, the height of said rebound being relatable to a known hardness value by means of said indicia; and
   a collector, a base and means for rotatably mounting said collector on said base, said tubular element being mounted on said collector, said passage means extending through said collector and said base with said opening being in said base, said collector and said base being relatively rotatable to displace said opening from said passage means and to permit said base to at least partially close off the lower end of said passage means.

2. A hardness tester as defined in claim 25 wherein said retaining means for said ball includes means defining an aperture centrally located with respect to said passage means, a movable ball release, and means on said ball release for carrying said ball, said ball release being movable to place said ball in registry with said aperture whereby the ball falls through said aperture and said passage means.

3. A hardness tester for testing the hardness of a surface of a tester specimen, said hardness tester comprising:
   a tubular element having upper and lower ends;
   means for mounting the tubular element in a generally upright position;
   a ball;
   means on said tubular element for releasably retaining said ball above said lower end;
   passage means extending from said retaining means through the tubular element and terminating in an opening adapted to be positioned over the surface of the test specimen;
   said tubular element having a wall through which the passage means is visible from the exterior of the tubular element and indicia on said wall;
   said ball having a lesser cross-sectional area than said passage means below the retaining means and a lesser cross-sectional area than said opening whereby the ball is sized to pass completely through said opening and when the ball is released from the retaining means, it falls by gravity through the passage means without touching the wall of the passage means and contacts the surface of the test specimen and rebounds from such surface, the height of said rebound being relatable to a known hardness value by means of said indicia;

said mounting means including a base and means for mounting said tubular element on said base for movement relative to said base, said base having said opening therein and said tubular element being movable between a first position in which the passage means terminates in said opening and a second position in which the passage means is spaced from said opening; and means for resiliently preloading said base mounting means against said base.

4. A hardness tester as defined in claim 3 wherein said opening includes a ramp on said base adjacent said opening for facilitating the collection of said ball from the surface of the test specimen.

5. A hardness tester for testing the hardness of a surface of a test specimen, said hardness tester comprising:

a tubular element having upper and lower ends;
means for mounting the tubular element in a generally upright position;
a ball;
means on said tubular element for releasably retaining said ball above said lower end;
passage means extending from said retaining means through the tubular element and terminating in a opening adapted to be positioned over the surface of the test specimen;
said tubular element having a wall through which the passage means is visible from the exterior of the tube and indicia on said wall;
said ball having a lesser cross-sectional area than said passage means below said retaining means whereby the ball can be released from the retaining means and fall by gravity through the passage means without touching the wall of the passage means and contact the surface of the test specimen, said ball being allowed to rebound from the surface of the test specimen with the height of the rebound being relatable to a known hardness value by said indicia;
said retaining means including a ball release, means for mounting said ball release for movement relative to said tube, means defining an aperture located centrally with respect to said passage means, and means on said ball release for carrying said ball, said ball release being movable to bring said ball into registry with said aperture whereby the ball falls through said aperture and said passage means to the surface of the test specimen; and
said aperture widening as it extends downwardly.

6. A hardness tester as defined in claim 5 wherein said ball release mounting means mounts the ball release for rotational movement.

7. A hardness tester as defined in claim 5 wherein said ball release mounting means mounts said ball release for translation.

8. A hardness tester as defined in claim 5 wherein said tubular element mounting means includes a base and means for mounting said tubular element on said base for movement relative to said base, said base having said opening therein and said tubular element being movable between a first position in which the passage means terminates in said opening and a second position in which the passage means is spaced from said opening.

9. A hardness tester for testing the hardness of a surface of a test specimen, said hardness tester comprising:

a tubular element having upper and lower ends;
means for mounting the tubular element in a generally upright position;
a ball;
means on said tubular element for releasably retaining said ball above said lower end;
passage means extending from said retaining means through the tubular element and terminating in an opening adapted to be positioned over the surface of the test specimen;
said tubular element having a wall through which the passage means is visible from the exterior of the tube and indicia on said wall;
said ball having a lesser cross-sectional area than said passage means below said retaining means whereby the ball can be released from the retaining means and fall by gravity through the passage means without touching the wall of the passage means and contact the surface of the test specimen, said ball being allowed to rebound from the surface of the test specimen with the height of the rebound being relatable to a known hardness value by said indicia;
said retaining means including a ball release, means for mounting said ball release for movement relative to said tube, means defining an aperture located centrally with respect to said passage means, and means on said ball release for carrying said ball, said ball release being movable to bring said ball into registry with said aperture whereby the ball falls through said aperture and said passage means to the surface of the test specimen; and
a collector, a base and means for rotatably mounting said collector on said base, said tubular element being mounted on said collector, said passage means extending through said collector and said base with said opening being in said base, said collector and said base being relatively rotatable to displace said opening from said passage means and to permit said base to at least partially close off the lower end of said passage means.

10. A hardness tester for testing the hardness of a surface of a test specimen, said hardness tester comprising:

a tubular element having upper and lower ends;
means for mounting the tubular element in a generally upright position;
a ball;
means on said tubular element for releasably retaining said ball above said lower end;
passage means extending from said retaining means through the tubular element and terminating in an opening adapted to be positioned over the surface of the test specimen;
said tubular element having a wall through which the passage means is visible from the exterior of the tubular element and indicia on said wall;
said ball having a lesser cross-sectional area than said passage means below the retaining means whereby when the ball is released from the retaining means, it falls by gravity through the passage means without touching the wall of the passage means and contacts the surface of the test specimen and rebounds from such surface, the height of said rebound being relatable to a known hardness value by means of said indicia;
said mounting means includes a base and means for mounting said tubular element on said base for movement relative to said base, said base having said opening therein and said tubular element being movable between a first position in which the passage means terminates in said opening and a second position in which the passage means is spaced from said opening; and said tubular element mounting means including a collector and means for rotatably mounting said collector and means for rotatably mounting said collector on said base, said passage means extending through said collector and said base, said collector and said base being relatively rotatable to displace said opening from said passage means and to permit said base to at least partially close off the lower end of said passage means.

11. A hardness tester as defined in claim 10 including resilient means for preloading said collector against said base.

12. A hardness tester for testing the hardness of a surface of a test specimen, said hardness tester comprising:

a tubular element having upper and lower ends;

means for mounting the tubular element in a generally upright position;

a ball;

means on said tubular element for releasably retaining said ball above said lower end;

passage means extending from said retaining means through the tubular element and terminating in an opening adapted to be positioned over the surface of the test specimen;

said tubular element having a wall through which the passage means is visible from the exterior of the tubular element and indicia on said wall;

said ball having a lesser cross-sectional area than said passage means below the retaining means whereby when the ball is released from the retaining means, it falls by gravity through the passage means without touching the wall of the passage means and contacts the surface of the test specimen and rebounds from such surface, the height of said rebound being relatable to a known hardness value by means of said indicia;

said mounting means includes a base and means for mounting said tubular element on said base for movement relative to said base, said base having said opening therein and said tubular element being movable between a first position in which the passage means terminates in said opening and a second position in which the passage means is spaced from said opening; and said tubular element mounting means having a region which is aligned with said opening of said base in said second position, said opening in said base being visible through said region in said second position.

* * * * *